United States Patent [19]

McRae et al.

[11] 4,233,980

[45] Nov. 18, 1980

[54] HEMOSTATIC COMPRESSIVE DEVICE

[75] Inventors: Lorin P. McRae; Mark M. Kartchner, both of Tucson, Ariz.

[73] Assignee: Narco Scientific Industries, Inc., Fort Washington, Pa.

[21] Appl. No.: 967,992

[22] Filed: Dec. 11, 1978

Related U.S. Application Data

[63] Continuation of Ser. No. 774,682, Mar. 7, 1977, abandoned.

[51] Int. Cl.³ .............................................. A61B 17/12
[52] U.S. Cl. .................................................... 128/325
[58] Field of Search ................ 128/155, 325, 327, 361

[56] References Cited

U.S. PATENT DOCUMENTS

| | | | |
|---|---|---|---|
| 3,171,410 | 3/1965 | Towle | 128/155 |
| 3,625,219 | 12/1971 | Abrams et al. | 128/325 |
| 3,633,567 | 1/1972 | Sarnoff | 128/327 |
| 3,669,118 | 6/1972 | Colon-Morales | 128/361 |
| 3,756,239 | 9/1973 | Smythe | 128/327 |
| 3,779,249 | 12/1973 | Semler | 128/325 |

FOREIGN PATENT DOCUMENTS 248153 12/1969 U.S.S.R. .................................. 128/325

*Primary Examiner*—Dalton L. Truluck
*Attorney, Agent, or Firm*—Browning, Bushman & Zamecki

[57] ABSTRACT

Disclosed is an inflatable bladder and a pressure plate which may be selectively positioned to hold the bladder so as to apply pressure to a blood vessel, for example. The bladder includes two sheets of flexible, non-elastic material. Expansion of the bladder may occur by inflation to separate the two sheets and press them outwardly against the pressure plate and the area of the subject to be compressed. An adjustable holder maintains the pressure plate in position. Pressure within the bladder may be monitored as an indication of the pressure exerted against the subject. Both the bladder and the pressure plate may be generally transparent to permit visual inspection and monitoring of the area being compressed.

16 Claims, 3 Drawing Figures

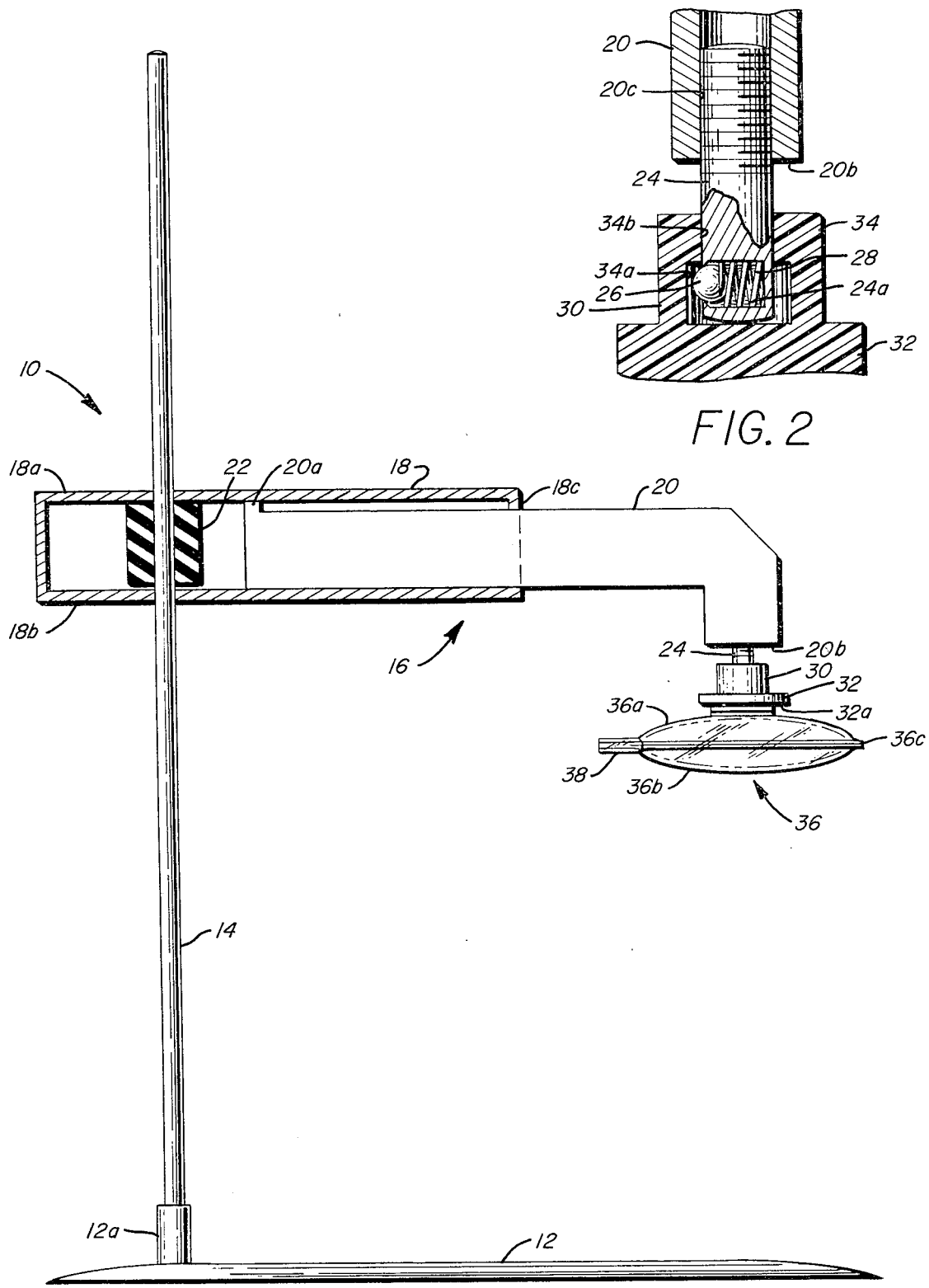

HEMOSTATIC COMPRESSIVE DEVICE

This is a continuation of application Ser. No. 774,682, filed Mar. 7, 1977, now abandoned.

BACKGROUND OF THE INVENTION

1. Field of the Invention

This invention pertains to apparatus for applying pressure to localized areas. More particularly, this invention relates to non-invasive techniques for applying uniformly distributed measured pressure over a blood vessel, such as the common femoral artery of a human subject or other arteries similarly inaccessible to normal pressure cuff compression, or for applying controlled non-occlusive pressure to produce hemostasis after arterial puncture.

2. Description of Prior Art

Current techniques for effecting non-invasive compression of arteries include the use of pressure cuffs. Such a cuff features a strip of non-elastic material to be wrapped around a limb. An elastic inflatable bladder is superimposed on the non-elastic material. When the bladder is inflated, usually pneumatically, pressure exerted by all parts of the enwrapment on the limb is increased. U.S. Pat. No. 3,171,410 discloses a pneumatic dressing of the pressure cuff type.

Also known is a C-clamp featuring a rigid footplate, and vertical positioning adjustment only, as shown, for example, in U.S. Pat. No. 3,779,249. Such apparatus may be used to exert non-calibrated and unevenly distributed pressure to the body surface overlying an artery.

U.S. Pat. No. 3,625,219 discloses a transparent rubber membrane clamped to a transparent plastic plate to form an expandable pressure chamber. Clamping screws are used to maintain various members of the chamber support structure in place, and must be loosened to adjust the position of the chamber relative to the area to which pressure is to be applied. U.S.S.R. Pat. No. 248,153 discloses an inflatable air balloon maneuverable on sliding bars.

SUMMARY OF THE INVENTION

The present invention includes an inflatable bladder formed with two sheets of transparent, non-elastic material providing inherent lateral restraint with vertical expansion accomplished by the separation of the two sheets of material due to inflation. The bladder may be mounted on a pressure plate by quick connect/disconnect means, such as a pair of adhesive patches fixed to the bladder and the pressure plate. The pressure plate, which is also constructed of transparent material, may be mounted on a positioning arm by second quick connect/disconnect means, such as a spring-biased snap-lock connector. This second connector device allows full rotation of the pressure plate, in a generally horizontal plane, relative to the positioning arm.

The positioning arm includes a housing and a horizontal sliding arm mounted for telescopic movement relative to the housing. Thus, the length of the positioning arm may be selectively adjusted by extension of the sliding arm out of the housing, or contraction of the sliding arm into the housing. The snap-lock connector mounts the pressure plate on the exposed end of the sliding arm. With the inflated bladder in pressure contact with a subject, upward force on the external end of the sliding arm results in torque applied to the sliding arm, effecting frictional locking between the sliding arm and the interior of the housing to prevent undesired variation in the length of the positioning arm. The locking of the sliding arm relative to the housing may be released by application of a downward force on the sliding arm, for example.

A combination of a platform and a vertical support pole joined thereto provides a base for locating and supporting the positioning arm. The support pole passes through the housing and is surrounded therein by a rubber sleeve. The housing may be selectively rotated in a plane perpendicular to the axis of the support pole, and selectively moved along the pole, in a vertical direction, for example. A frictional lock between the pole and the housing is provided by the rubber sleeve and the relatively close fit of the pole within the passages through the housing walls. Thus, as force is applied at the distal end of the positioning arm by pressure contact of the inflated bladder with a subject, the resulting torque about the pole/housing junction prevents undesired rotational or translational movement of the housing relative to the pole. The locking between the housing and the pole is released by application of counter torque about the pole/housing junction, for example. Frictional forces between the pole and rubber sleeve resist movement of the housing relative to the pole, but can be overcome as desired by sufficient hand-generated force, for example.

The present invention thus provides an inflatable, transparent bladder, and a transparent pressure plate, mounted on support apparatus whereby at least three degress of freedom are available to the pressure plate and bladder. Thus, for example, the pressure plate and bladder, mounted on the end of the sliding arm, may be moved vertically along the pole, horizontally around the pole, and horizontally toward and away from the pole. The aforementioned friction locking mechanisms act to retain the sliding arm and housing fixed against unwanted movement relative to the pole due to forces exerted on the pressure plate. However, the friction locking mechanisms may be readily released to effect movement of the sliding arm as desired. Thus, the sliding arm, with pressure plate and bladder attached, may be readily maneuvered in the three degrees of freedom to position the bladder over the area to be compressed. The bladder may be readily removed from, and, if desired, returned to the compression area as needed. Similarly, the pressure plate is easily joined to or released from the sliding arm, and the bladder is likewise easily attached to or disconnected from the pressure plate.

The detachable bladder may be sterilized to provide an aseptic barrier between the compression area of the subject and the pressure plate. During a surgical procedure, for example, the bladder, which may be disposable, may be quickly replaced with a sterile, new bladder as needed.

Although use of the present invention is not limited in application to compression of the femoral artery, compression of this specific artery in human subjects provides an example of the advantageous implementation of the present invention. A pressure cuff cannot normally be applied in such a way as to compress the common femoral artery. A C-clamp device with a solid footplate has been used for applying pressure to the common femoral artery, but without calibration or uniform distribution of this pressure. Also, the entire C-clamp has to be manipulated and particularly moved from side to side in order to be positioned to apply pressure to the common femoral arteries. The present invention provides a compressive device wherein the applied pressure may be uniformly applied over a selected area by means of the flexible bladder rather than a cuff, and may be monitored by observation of the pressure within the bladder. Ease and flexibility of positioning the bladder of the present invention are increased compared to the prior art, and the transparency of the bladder and pressure plate allows full visualization of the surface of the subject being compressed.

BRIEF DESCRIPTION OF THE DRAWINGS

FIG. 1 is a side elevation in partial section of a compressive device according to the present invention;

FIG. 2 is a fragmentary view in partial section of the pressure plate and snap-lock, showing the manner in which the pressure plate is secured to the sliding arm.

DESCRIPTION OF PREFERRED EMBODIMENT

Figure 3:
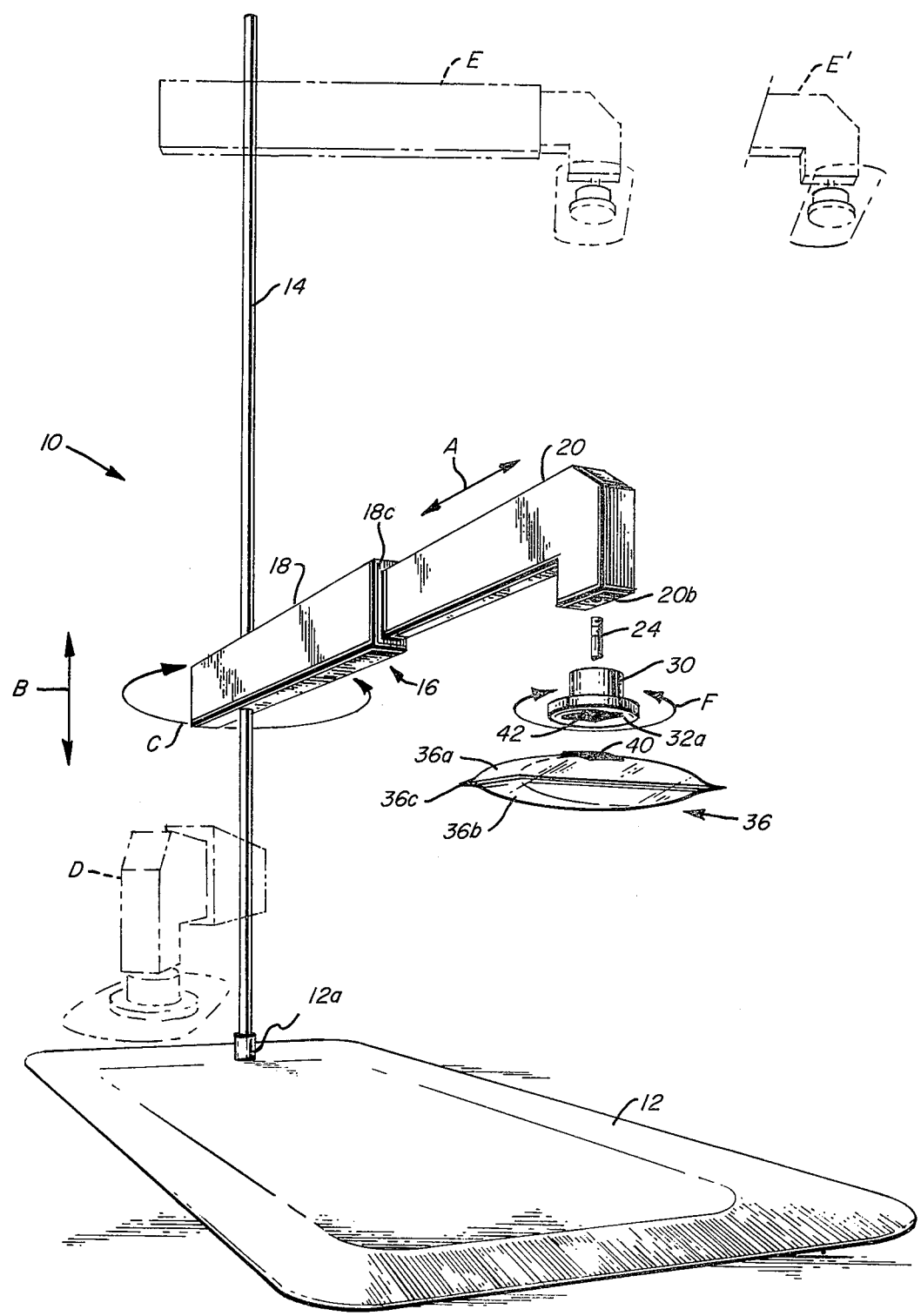
FIG. 3 is a partially exploded view in perspective of the compressive device, with mobility of the arm indicated by arrows as well as views in phantom.

A compressive device according to the present invention is shown generally at 10 in FIGS. 1 and 3, with further detail illustrated in FIG. 2. A platform 12 serves as a foundation for the apparatus. A support pole 14 may be rigidly joined to the platform 12 by means of threaded engagement between the pole and an internally threaded socket 12a as part of the platform, for example. Together, the platform 12 and pole 14 act as a base for supporting the apparatus.

An adjustable positioning arm, shown generally at 16, includes an elongate housing 18 and a sliding arm 20. The housing 18 is generally rectangular in vertical cross section, and includes upper and lower walls 18a and 18b respectively. The support pole 14 passes through mutually aligned holes in the housing walls 18a and 18b. Within the housing 18, the pole 14 passes through a sleeve 22 of resilient material, such as rubber, exhibiting a relatively high coefficient of friction with the pole. The sleeve 22 generally extends the distance between the housing walls 18a and 18b, and fits relatively tightly around the pole 14 for a purpose discussed hereinafter. Similarly, the holes in the housing walls 18a and 18b through which the pole 14 passes are small enough to provide a close fit about the pole, as discussed more fully hereinafter.

The sliding arm 20, which is also generally of rectangular cross section, features a first end with an upwardly directed rim 20a. The sliding arm 20 is received through an open end of the housing 18 and moves within the housing in telescoping fashion. The open end of the housing 18 features a downwardly extending rim 18c which, in combination with the bottom wall 18b of the housing, defines a closely fitting opening for passage of the sliding arm 20 therethrough. As indicated by a double-ended arrow A in FIG. 3, the sliding arm 20 may be adjusted by translational movement of the arm 20 relative to the housing 18 to further extend beyond the housing, or to be retracted farther within the housing. The sliding arm rim 20a rides along the inner surface of the upper housing wall 18a as the bottom surface of the sliding arm moves in contact with the inner surface of the lower housing wall 18b. Similarly, the side walls of the housing 18 enclose the sliding arm 20 within the housing. Thus, the sliding arm 20 is generally constrained against lateral and rotational movement relative to the housing 18.

As the sliding arm 20 is extended outwardly beyond the housing 18, the sliding arm rim 20a may eventually contact and be stopped by the housing rim 18c. The combination of the two rims 18c and 20a serves to limit the movement of the sliding arm 20 longitudinally out of the housing 18. However, by lifting the extended sliding arm 20 in a pivoting motion about the location of the two rims 18c and 20a, the sliding arm may be withdrawn from the housing as the sliding arm rim 20a passes under the housing rim 18c. Similarly, the sliding arm 20 may be mounted within the housing 18 by inserting the sliding arm first end with the rim 20a behind the housing rim 18c and reversing the pivotal motion by rotating the sliding arm downwardly from an upwardly oriented position to align the longitudinal axis of the sliding arm parallel to that of the housing 18. Then, the sliding arm 20 may be moved longitudinally into the housing 18.

The second end of the sliding arm 20 features a 90° elbow and a downwardly facing surface 20b. An upwardly-directed threaded bore 20c passes through the surface 20b and receives the threaded end of a shaft 24 (FIG. 2). The opposite end of the shaft features a spring-biased snap-lock device, including a ball locking element 26 maintained within a laterally extending chamber 24a within the shaft. The diameter of the ball 26 is slightly less than that of the cross section of the chamber 24a, but is greater than that of a side opening in the shaft 24 at one end of the chamber. A coil spring 28 urges the ball 26 toward the chamber opening, whereby the ball is made to partially protrude beyond the outer surface of the shaft 24. The ball 26 and coil spring 28 may be positioned within the chamber 24a in a conventional manner. For example, the spring may be threaded through the aforementioned opening of the chamber, and the ball inserted through an additional side opening not normally exposed to the ball for exit therethrough under influence of the spring. Such an opening is not shown, and such construction and assembly techniques, being known, are not further discussed herein.

A pressure plate 30 includes a laterally extending base 32 with a bottom surface 32a, and a generally tubular trunk 34. The trunk 34 includes a cylindrical chamber 34a communicating through the end of the trunk by a passage 34b of lesser cross-sectional diameter than the chamber 34b. The passage 34b may receive the shaft 24, the ball 26 being forced against the spring 28 within the chamber 24a by the interior surface of the passage 34b. The vertical longitudinal dimension of the chamber 34a is sufficient to accommodate the end of the shaft 24 so that the ball 26, biased outwardly by the spring 28, may again protrude beyond the lateral extent of the shaft 24 as well as that of the passage 34b. In this configuration, the spring-biased protruding ball 26 latches under the interior shoulder marking the junction of the chamber 34a with the passage 34b to lock the pressure plate 30 onto the shaft 24. The shaft 24 may be withdrawn from within the interior of the trunk 34 with the ball 26 again being forced against the spring 28 within the chamber 24a by the interior surface of the passage 34b. The combination of the snap-lock, including the ball 26 and the spring 28, and the chamber 34a and passage 34b within the trunk of the pressure plate 30 thus serves as a quick connect/disconnect device whereby the pressure plate may be readily mounted onto the shaft, or disengaged therefrom. The force constant of the spring 28 is sufficient to maintain the ball 26 protruding beyond the lateral extent of the passage 34b to retain the pressure plate 30 connected to the shaft 24, but the pressure plate may be removed from the shaft as desired by a sufficient pull on the pressure plate to force the ball against the spring for movement through the passage 34b.

An inflatable bladder shown generally at 36 includes upper and lower sheets of flexible, non-elastic material 36a and 36b. The two sheets 36a and 36b are generally oblong in shape, and are joined together along their respective peripheries to form a seam 36c. A tube 38 is sealingly anchored to the bladder 36 at a position along the seam 36c, and communicates with the interior of the bladder. The tube 38 thus forms a terminal by which external apparatus (not shown) may be joined to the bladder 36, and by which fluid pressure may be communicated for the purposes of inflating and deflating the bladder. The tube 38 may be composed of any of a variety of materials, such as rubber, for communicating fluid pressure and for accommodating a friction coupling with tubing, for example, leading to the external pressure apparatus.

The top bladder sheet 36a may be fitted with a patch of adhesive material 40. A similar patch of adhesive material 42 may be positioned on the pressure plate bottom surface 32a. Thus, the bladder 36 may be mounted on the pressure plate 30 by simply bringing these two elements together so that the two adhesive patches 40 and 42 contact. Any suitable material which adheres on contact may be used to join the bladder 36 to the pressure plate 30. For example, the commonly known fastening material sold under the trademark VELCRO may be used to form the patches 40 and 42. The nature of the VELCRO material is such that two VELCRO patches will mutually adhere by simply being brought into contact with but slight pressure. The VELCRO patches may be separated by being pulled apart.

The patch 40 is bonded to the bladder sheet 36a with the adhering patch surface exposed. The patch 42 is similarly bonded to the pressure plate bottom surface 32a with the adhering patch surface exposed. Thus the bladder 36 may be mounted on the pressure plate 30 by simply pressing these two elements together with the patches 40 and 42 in mutual contact. Also, the bladder 36 may be disconnected from the pressure plate 30 by a pull to separate the two patches 40 and 42. Consequently, such patches 40 and 42 provide a quick connect/disconnect union between the bladder 36 and the pressure plate 30.

The bladder sheets 36a and 36b are not only flexible but are impervious to at least low pneumatic pressure. Further, the sheets are generally transparent in the visible range of the electromagnetic spectrum. Similarly, the pressure plate 30 is also composed of material generally transparent in the visible spectrum.

As pneumatic pressure is communicated to the interior of the bladder 36, the bladder inflates by expansion generally along the direction perpendicular to the plane of the seam 36c. Thus, inflation occurs by general separation of the two bladder sheets 36a and 36b.

With the bladder 36 and pressure plate 30 mounted as illustrated in FIG. 1, the platform 12 and the positioning arm at 16 may be manipulated to position the bladder generally over a selected area to which pressure is to be applied. In the case of a human subject, for example, the platform 12 may be inserted between the subject and the table or other facility supporting the subject. The positioning arm at 16 may then be manipulated by hand along and about the support pole 14, as indicated by double-ended arrows B and C, respectively, in FIG. 3, until the housing 18 is directed generally toward a position just above the area to be compressed. The relatively tight friction grip of the sleeve 22 on the pole 14 serves to anchor the housing 18 against rotational as well as translational motion relative to the pole. Thus, the sleeve 22 which is held between the upper and lower housing walls 18a and 18b, respectively, acts to grip the pole 14 and thereby support and anchor the housing 18 relative to the pole. This friction anchoring may be overcome by hand pressure, for example, to selectively manipulate the housing along and about the pole 14.

It will be appreciated that the bladder 36 may be located at an infinite number of positions relative to the pole 14 and platform 12. Two additional configurations of the positioning arm 16 are indicated in phantom at D and E in FIG. 3 to illustrate this flexibility of positioning of the bladder 36. Further, the extension of the positioning arm 16 by telescopic movement of the sliding arm 20 relative to the housing 18 to locate the bladder 36 is also indicated in phantom at E'.

The sliding arm 20 may be telescoped into or out of the housing 18 as needed to position the pressure plate 30 and bladder 36 as required. With the bladder 36 at least partially inflated and in contact with the subject and applying modest pressure, an upwardly directed reaction force is exerted through the pressure plate 30 to the sliding arm 20. As a result, a torque is applied to the sliding arm 20 relative to its connection with the housing 18, and, in turn, a torque is applied to the housing 18 relative to its junction with the vertical pole 14. Thus, the sliding arm 20 is pressed upwardly against the rim 18c of the housing and downwardly against the interior surface of the bottom wall of the housing 18b to prevent unwanted slippage of the sliding arm relative to the housing 18. Similarly, the upward force exerted by the sliding arm 20 on the rim 18c tends to urge the housing 18 to rotate in a vertical plane about the connection between the housing and the pole 14. However, as noted hereinbefore, the holes in the housing walls 18a and 18b through which the pole 14 passes provide a relatively tight fit between the housing walls and the pole. Consequently, any tendency of the housing 18 to rotate in a vertical plane relative to the pole 14 is resisted by the interaction between the housing walls 18a and 18b and the pole. Further, since the walls 18a and 18b are pressed against the pole as a result of any torque urging the housing 18 to rotate in a vertical plane, the housing and, consequently, the entire positioning arm at 16 is further locked against rotation about the pole as well as translation along the pole when such upward force is applied to the pressure plate 30. The effect of the torque thus generated is to provide a releasable friction lock between the housing 18 and the sliding arm 20 to anchor the latter against telescopic movement relative to the housing, and to provide a second releasable friction lock between the pole 14 and the housing to prevent movement of the housing relative to the pole. Therefore, while the combination of the positioning arm at 16 and the pole 14 provides for maneuverability of the pressure plate 30 and bladder 36 according to three degrees of freedom, as indicated by the double-ended arrows A, B, and C in FIG. 3, the positioning arm is constructed to lock into position as set, particularly when the bladder 36 is in contact with, and applying pressure on, a subject.

The snap-lock connection between the pressure plate 30 and the shaft 24, which serves to fasten the pressure plate to the positioning arm at 16, also provides an additional degree of freedom for the pressure plate relative to the sliding arm 20. Thus, as indicated by the double-ended arrow F, the pressure plate 30, and the bladder 36 attached thereto, may be freely rotated about the shaft 24 and, therefore, relative to the second end of the sliding arm 20. This rotation of the pressure plate and bladder about the longitudinal axis of the shaft 24 may occur without disconnecting the ball snap-lock.

In a typical application on a human subject, for example, the transparent, inflatable bladder 36 is placed over the common femoral artery generally in a transverse rotation relative to the inguinal ligament, at the location where the common femoral passes over the superior ramus of the pubis. With the platform 12 in position relative to the subject as described, the pressure plate 30 is attached by the snap-lock to the positioning arm, which is elevated, rotated, extended, retracted or lowered as necessary so that the pressure plate may be attached to the bladder and may then exert a modest pressure upon the uniflated bladder. A standard means (not shown) can then be used to apply pneumatic pressure to inflate the bladder through the tube 38, and to monitor the pressure of inflation.

The flexibility of the sheets 36a and 36b of the inflated bladder pressing on the subject insures that a uniform pressure is applied to the subject over an extended area. Thus, for example, a puncture site and the adjacent body surface may be subjected to the same controlled and monitored pressure, applied uniformly over the area in question contacted by the bottom bladder sheet 36b.

As long as the vertical deflection of the bladder sheets is restrained by the pressure plate and the surface of the subject body, the pressure within the bladder is an accurate indication of the pressure being exerted uniformly on the surface of the subject body overlying the femoral artery or any other area of application. Similarly, as long as the bladder remains inflated with the upper and lower sheets separated, pressure within the bladder and, therefore, on the body's surface may be increased by a downward displacement of the pressure plate while the rise in bladder pressure is monitored. This downward motion of the pressure plate may be effected by hand-manipulating the housing 18 down the pole 14 as required. The upward force of the pressure plate on the horizontal sliding arm 20 creates a torque which locks all sliding mechanisms and prevents further vertical, horizontal, or rotational displacement.

The pressure on the subject may also be increased by communicating increased fluid pressure to the bladder through the tube 38. Thus, any value of pressure may be uniformly applied to the subject, and monitored at the same time.

The transparency of the bladder and the pressure plate allows the body surface being compressed to be visually monitored. Where compression by the bladder is being utilized to effect hemostasis after arterial puncture, the pulsations and/or bleeding at the puncture site can thus be observed through the bladder and the pressure plate.

The contact union between the bladder and the pressure plate by means of the adhesive patches 40 and 42 permits the bladder to be quickly connected to the pressure plate as well as to be quickly removed therefrom. Consequently, the bladder and pressure plate may both be assembled in conjunction with the positioning arm at 16 in the course of rapid, emergency use. Furthermore, the bladder, which is disposable and can be sterilized, may be quickly replaced with a fresh, sterile bladder during a surgical procedure. The sterile bladder itself acts as an aseptic barrier between the area being compressed, such as a puncture site, and the pressure plate.

It will be appreciated that the present invention provides apparatus for the sphygmomanometric occlusion of the common femoral artery and other arteries of the body that are not commonly amenable to cuff occlusion when taking indirect blood pressure. Further, with the present invention, a controlled pressure may be maintained over a puncture site upon the withdrawal of a catheter at the termination of percutaneous arterial catheterization or other procedures involving arterial puncture to facilitate sealing of the arterial puncture site and elimination of post-catheterization bleeding and hematoma. Similarly, the present invention may be used to apply controlled pressure over the puncture site following renal dialysis to achieve hemostasis at the renal dialysis access puncture.

The present invention provides a sterile, disposable, transparent, inflatable pressure bladder for application over an arterial puncture site with direct visualization through the bladder as well as through the connected pressure plate to confirm proper placement as well as hemostasis. Further, a positioning and retaining structure is provided which allows quick, three-dimensional placement of the pressure plate relative to the inflatable bladder without requiring movement of the structure base, or the patient. Further, quick and secure connecting devices are provided to mount the pressure plate on the positioning arm and to mount the bladder on the pressure plate. Apparatus of the present invention may also be modified to allow a bed, stretcher, or other procedure table to serve as the foundation for anchoring the support pole.

The foregoing disclosure and description of the invention is illustrative and explanatory thereof, and various changes in the size, shape and materials as well as in the details of the illustrated construction may be made within the scope of the appended claims without departing from the spirit of the invention.

We claim:

1. Apparatus for applying pressure to areas comprising:
    (a) bladder means including a first sheet of generally non-elastic flexible material and a second sheet of generally non-elastic flexible material, said first and second sheets being mutually connected about their respective peripheries, wherein said bladder means is inflatable to expand by the mutual separation of the interior regions of said two sheets generally along the direction in which pressure is to be applied to such area;
    (b) pressure plate means for contacting one of said sheets for constraining said bladder means;
    (c) support means for supporting said pressure plate means, including base means and positioning arm means for mounting thereon whereby said pressure plate means may be selectively positioned;
    (d) housing means, as part of said positioning arm means, including generally opposed first and second elongate wall means, joined to said base means and selectively moveable, relative thereto, translationally and rotationally;

(e) sliding arm means, as part of said positioning arm means, telescopically moveable generally between and along said first and second wall means whereby said positioning arm means is selectively extensible, and to which said pressure plate means may be selectively connected;

(f) first selectively releasable lock means, including sleeve means positioned between said first and second wall means and frictionally engaging said base means, for selectively maintaining said housing means fixed against motion relative to said base means; and (g) second selectively releasable lock means, including frictional engagement between at least one of said first and second wall means and said sliding arm means, for selectively maintaining said sliding arm means fixed against motion relative to said housing means.

2. Apparatus as defined in claim 1 further comprising snap-lock means for selectively connecting said pressure plate means to said sliding arm means.

3. Apparatus as defined in claim 2 further comprising adhesive connector means for selectively connecting said bladder means to said pressure plate means.

4. Apparatus as defined in claim 3 wherein said adhesive connector means comprises first and second patches of VELCRO material fixed to said bladder means and to said pressure plate means, respectively.

5. Apparatus as defined in claim 2 wherein said snap-lock means comprises spring-biased lock means.

6. Apparatus as defined in claim 1 further comprising adhesive connector means for selectively connecting said bladder means to said pressure plate means.

7. Apparatus as defined in claim 6 wherein said adhesive connector means comprises first and second patches of VELCRO material fixed to said bladder means and to said pressure plate means, respectively.

8. Apparatus as defined in claim 1 wherein said first and second sheets are generally transparent.

9. Apparatus as defined in claim 8 wherein said pressure plate means is generally transparent.

10. Apparatus as defined in claim 1 further comprising terminal means joined to said bladder means for communicating fluid pressure to and from the interior of said bladder means.

11. Apparatus for applying pressure to areas comprising:

(a) inflatable bladder means;

(b) pressure plate means for maintaining said bladder means in position;

(c) positioning arm means for supporting and selectively positioning said pressure plate means wherein said positioning arm means is selectively extensible to vary the length thereof;

(d) base means, including generally elongate pole means for supporting said positioning arm means, said pole means and said positioning arm means mutually engagable by first releasable friction lock means, including sleeve means for frictionally engaging said pole means, whereby said positioning arm means is selectively moveable translationally and rotationally relative to said pole means, and is selectively releasably locked against such movement relative to said pole means;

(e) housing means, as part of said positioning arm means, engagable to said pole means by said first friction lock means, and including generally opposed first and second elongate housing walls; and (f) sliding arm means, as part of said positioning arm means, telescopically moveable relative to said housing means generally between said first and second housing walls whereby said positioning arm means is selectively extensible, said housing means and said sliding arm means mutually engagable by second releasable friction lock means including said sliding arm means frictionally engaging at least one of said first and second housing walls, and including the end of at least one of said first and second housing walls frictionally engaging said sliding arm means, whereby said sliding arm means is selectively moveable longitudinally relative to said housing means and is selectively, releasably locked against such movement relative to said housing means by such frictional engagements.

12. Apparatus as defined in claim 11 further comprising snap-lock means for selectively connecting said pressure plate means to said sliding arm means.

13. Apparatus as defined in claim 11 further comprising adhesive connector means for selectively connecting said bladder means to said pressure plate means.

14. Apparatus as defined in claim 13 wherein said adhesive connector means comprises first and second patches of VELCRO material fixed to said bladder means and to said pressure plate means, respectively.

15. Apparatus as defined in claim 11 wherein said bladder means comprises a first sheet of generally non-elastic flexible material and a second sheet of generally non-elastic flexible material, said first and second sheets being mutually connected about their respective peripheries, wherein said bladder means is inflatable to expand by the mutual separation of the interior regions of said two sheets generally along the direction in which pressure is to be applied to such area.

16. Apparatus as defined in claim 15 further comprising terminal means joined to said bladder means for communicating fluid pressure to and from the interior of said bladder means.

* * * * *